United States Patent [19]

Noseworthy

[11] 3,957,980

[45] May 18, 1976

[54] DOXYCYCLINE PARENTERAL COMPOSITIONS

[75] Inventor: Melvin M. Noseworthy, Gales Ferry, Conn.

[73] Assignee: Pfizer Inc., New York, N.Y.

[22] Filed: June 10, 1974

[21] Appl. No.: 477,703

Related U.S. Application Data

[63] Continuation-in-part of Ser. No. 301,326, Oct. 26, 1972, abandoned.

[52] U.S. Cl. .............................................. 424/227
[51] Int. Cl.² ......................................... A61K 31/65
[58] Field of Search .................................. 424/227

[56] References Cited

UNITED STATES PATENTS

| | | | |
|---|---|---|---|
| 2,438,106 | 3/1948 | Alburn et al. | 424/365 |
| 3,459,854 | 8/1969 | Boissier et al. | 424/227 |
| 3,674,859 | 7/1972 | Beutel et al. | 424/227 |

Primary Examiner—Stanley J. Friedman
Attorney, Agent, or Firm—Connolly and Hutz

[57] ABSTRACT

Doxycycline compositions suitable for the preparation of injectable liquid preparations are disclosed.

10 Claims, No Drawings

DOXYCYCLINE PARENTERAL COMPOSITIONS

CROSS REFERENCE TO RELATED APPLICATION

This application is a continuation-in-part of my copending application Ser. No. 301,236, filed Oct. 26, 1972, now abandoned.

BACKGROUND OF THE INVENTION

This invention relates to antibiotic compositions suitable for parenteral administration. More particularly it relates to novel doxycycline parenteral compositions.

Because of the therapeutic importance of the tetracycline-type antibiotics, efforts have been made to prepare compositions suitable for parenteral administration. Aqueous solutions of doxycycline can be prepared in the highly acid or alkaline pH range, but these solutions are found objectionable due to their low stability and poor local tolerance upon injection. With the exception of polyvinylpyrrolidine compositions and Mannich base derivatives very little pharmaceutical technology has been developed for a parenteral form of doxycycline.

SUMMARY OF THE INVENTION

It has now been found that stable injectable solutions of doxycycline can be provided by means of a novel aqueous pharmaceutical composition comprising a solution in water of from about 1% to 10% by weight of an antibiotic compound selected from doxycycline and the pharmaceutically acceptable acid addition salts thereof, together with about 3 to 8 molar proportions of a phosphate selected from phosphoric acid, sodium or potassium orthophosphate, metaphosphate, pyrophosphate, tripolyphosphate or hexametaphosphate, and about 3 to 8 molar proportions of a pharmaceutically acceptable magnesium salt soluble in said aqueous pharmaceutical composition, said composition having a pH value in the range of from about 1.0 to 3.5.

A pharmaceutical composition suitable for reconstitution with water is also provided which comprises a pharmaceutically acceptable acid addition salt of doxycycline, together with about 3 to 8 molar proportions of a water-soluble alkali metal phosphate salt, wherein said alkali metal phosphate salt is sodium or potassium orthophosphate, metaphosphate, pyrophosphate, tripolyphosphate or hexametaphosphate, and about 3 to 8 molar proportions of a pharmaceutically acceptable water-soluble magnesium salt.

DETAILED DESCRIPTION OF THE INVENTION

Doxycycline, the therapeutically-active component of the novel pharmaceutical compositions of this invention, is a tetracycline-type antibiotic of high potency with excellent oral absorption characteristics and a superior half-life. It is particularly described in U.S. Pat. No. 3,200,149 under the chemical name, $\alpha$-6-deoxy-5-oxytetracycline. An effective concentration range for doxycycline in the aqueous solutions of this invention is generally from about 1 to 10% by weight of the total in the form of the free base or a pharmaceutically acceptable acid addition salt. Magnesium ions combine with doxycycline in solution to form magnesium-doxycycline chelates. Magnesium chloride is a convenient source of magnesium ions but other magnesium compounds useful for the purpose of this invention include magnesium oxide, magnesium sulfate, magnesium ascorbate, magnesium lactate and magnesium gluconate. The molar ratio of magnesium to doxycycline in these compositions is at least about 3:1. The preferred ratio is from about 3:1 to 8:1, with the especially preferred ratio being from about 3:1 to 4:1.

The doxycycline antibiotic component is used in the form of the free base or one of its pharmaceutically acceptable acid addition salts. Alternatively, if a preconstituted aqueous formulation is to be manufactured, the antibiotic component may be introduced as the free base and the acid salt formed in situ by addition of the appropriate acid which is used for the pH adjustment discussed below. Examples of suitable doxycycline acid addition salts which can be used for these purposes include each pharmaceutically acceptable acid addition salts as the hydrochloride, hydrobromide, sulfate, nitrate, ascorbate, citrate, gluconate, lactate, isonicotinate, gentisinate, pantothenate, salicylate, glucuronate, formate and glutamate, etc. The preferred acid addition salt is doxycycline hydrochloride, e.g., in the form of doxycycline hyclate, which is doxycycline hydrochloride hemiethanolate hemihydrate.

The pH value is adjusted to the preferred range of from about 1.0 to 3.5 by means of an acid that is pharmaceutically acceptable, such as ascorbic acid, tartaric acid, gluconic acid, glucuronic acid, citric acid, gentisic acid, isonicotinic acid, glutamic acid, and so forth. Of these compounds, ascorbic acid is preferred, since it also serves to act as an anti-oxidant for the mixture. In the case of a composition intended for reconstitution, a solid acid is used. When using higher doxycycline concentration, e.g. 80 mg/ml to 100 mg/ml, an acid buffer is not needed since the pH will be in the desired range from about pH 1.0 to 3.5. The especially preferred range, however, is from about pH 1.5 to 3.0.

As previously indicated, ascorbic acid may function as an anti-oxidant to enhance the stability of these aqueous solutions. However, other reducing substances such as sodium metabisulfite, sodium sulfite, sodium formaldehyde sulfoxylate, propyl gallate and monothioglycerol can also be used in this connection, if so desired, particularly when added to the system at concentration levels in the 0.1 to 1% weight range with respect to said solution.

A further component which may be utilized in the present composition with beneficial effect is a water-soluble local anesthetic. The most useful of these compounds are procaine, lidocaine and their respective hydrochloride salts. Other dialkylamino alkanol esters of p-aminobenzoic acid as the water-soluble salts, e.g. hydrochloride, are also useful for this purpose.

The compositions of this invention may be prepared by merely mixing the doxycycline base or acid addition salt with the desired proportions of the other ingredients. The ingredients can be mixed in powder form first and then dissolved in water shortly before administration, or a stable aqueous solution suitable for injection can be prepared and kept in stock until ready for use. In the case of the dry powder composition it is usually preferable to introduce all solid ingredients in finely divided form and to blend the mixture to obtain a uniform product. Standard pharmaceutical equipment may be used for this purpose. The mixture may also be milled if desired. However, prolonged high temperature should be avoided.

An essential component of this invention is a phosphate selected from a phosphoric acid in the case of the preconstituted composition and a water-soluble alkali metal salt, such as sodium or potassium orthophosphate, metaphosphate, pyrophosphate, tripolyphosphate or hexametaphosphate in the case of the powder composition. The preferred salt, however, is sodium orthophosphate, also known as sodium dihydrogen phosphate. The inclusion of a phosphate in the compositions of this invention provides effective blood levels of doxycycline, prevents gelling of the compositions when water is added and prevents the precipitation of doxycycline in blood serum. The molar ratio of a phosphate to doxycycline in these compositions is one that is in the range of at least about 3:1. The preferred ratio is from about 3:1 to 8:1, with the especially preferred ratio being from about 3:1 to 4:1.

In the following illustrative examples the doxycycline hydrochloride is employed in the form of the hemiethanolate hemihydrate (hyclate).

EXAMPLE I

A dry solid pharmaceutical composition was prepared by intimately blending 635.0 mg. of doxycycline hydrochloride with 641.77 mg. of magnesium chloride tetrahydrate, 529.7 mg. of sodium dihydrogen phosphate and 675.99 mg. of ascorbic acid. The blended powder thus obtained was then dissolved in 8.4 ml. of sterile water which brought the total volume to 10 ml. The resulting solution was found to have a pH value of 2.0. The solution remained fluid and clear for over 24 hours at room temperature.

Animal protection tests were carried out in mice against staphylococcus aureua 01A005 by intramuscular and intravenous administration. Results indicated that satisfactory protection was achieved by the use of this composition.

EXAMPLE II

Dry solid compositions may be prepared by substituting an equivalent molar amount of sodium metaphosphate, sodium pyrophosphate, sodium tripolyphosphate or sodium hexametaphosphate for the sodium dihydrogen phosphate contained in Example I.

EXAMPLE III

A mixture of the following materials was prepared:

|   | Mgs. |
|---|---|
| Doxycycline hydrochloride | 635.00 |
| Magnesium chloride.4H$_2$O | 641.77 |
| Sodium dihydrogen phosphate | 529.70 |
| Ascorbic acid | 675.99 |
| Lidocaine hydrochloride | 200.00 |

This composition was dissolved in 8.1 ml. of water provided a clear product with a pH of 2.0.

EXAMPLE IV

A mixture of the following materials was prepared:

|   | Mgs. |
|---|---|
| Doxycycline hydrochloride | 635.00 |
| Magnesium gluconate | 308.66 |
| Sodium dihydrogen phosphate | 529.70 |
| Ascorbic acid | 675.99 |

When this mixture was diluted with 8.0 ml. of water, a clear solution with pH 2.0 resulted.

EXAMPLE V

A mixture of the following materials was prepared:

|   | Mgs. |
|---|---|
| Doxycycline hydrochloride | 635.00 |
| Magnesium chloride.4H$_2$O | 855.69 |
| Sodium dihydrogen phosphate | 529.70 |
| Ascorbic acid | 655.8 |

This composition when dissolved in 8.0 ml. of water produced a clear solution with a pH of 2.0.

EXAMPLE VI

A mixture of the following materials was prepared:

|   | Mgs. |
|---|---|
| Doxycycline hydrochloride | 1,265.0 |
| Magnesium chloride.4H$_2$O | 1,755.9 |
| Sodium dihydrogen phosphate | 1,190.0 |

When this composition is dissolved in 8.2 ml. of water, a clear solution containing 100 mg/ml. of doxycycline activity results having a pH of 2.0.

EXAMPLE VII

A mixture of the following materials was prepared:

|   | Mgs. |
|---|---|
| Doxycycline hydrochloride | 127.55 |
| Magnesium chloride.4H$_2$O | 128.39 |
| Sodium dihydrogen phosphate | 105.94 |
| Ascorbic acid | 131.10 |

When this composition is dissolved in 8.3 ml. of water, a clear solution, having a pH of 2.0, and containing 10 mg/ml. of doxycycline activity is produced.

EXAMPLE VIII

A mixture of the following materials was prepared:

|   | Mgs. |
|---|---|
| Doxycycline hydrochloride | 255.10 |
| Magnesium chloride.4H$_2$O | 256.78 |
| Sodium dihydrogen phosphate | 211.88 |
| Ascorbic acid | 400.00 |

When this composition is dissolved in 9.4 ml. of water, a clear solution containing 20 mg/ml. of doxycycline activity is produced. The pH is 1.9.

EXAMPLE IX

A mixture of the following materials was prepared:

|   | Mgs. |
|---|---|
| Doxycycline hydrochloride | 1,020.40 |
| Magnesium chloride.4H$_2$O | 1,164.7 |
| Sodium dihydrogen phosphate | 960.7 |

When this composition is dissolved in 8.3 ml. of water, a clear solution containing 80 mg/ml. of doxycycline activity and having a pH of 1.66 is produced.

EXAMPLE X

A mixture of the following materials was prepared:

|  | Mgs. |
| --- | --- |
| Doxycycline hydrochloride | 635.00 |
| Magnesium chloride.4H$_2$O | 641.77 |
| Potassium dihydrogen phosphate | 522.3 |
| Ascorbic acid | 675.99 |

When this mixture was diluted with 8.5 ml. of water, a clear solution with pH 2.0 resulted.

EXAMPLE XI

A mixture of the following materials was prepared:

|  | Mgs. |
| --- | --- |
| Doxycycline hydrochloride | 635.00 |
| Magnesium chloride.4H$_2$O | 642.00 |
| Potassium dihydrogen phosphate | 522.00 |
| Citric acid | 3,570.00 |

When this composition is dissolved in 6.5 ml. of water, a clear solution containing 50 mg/ml of doxycycline activity and having a pH of 1.1 is produced.

EXAMPLE XII

A mixture of the following materials was prepared:

|  | Mgs. |
| --- | --- |
| Doxycycline hydrochloride | 635.00 |
| Magnesium chloride.4H$_2$O | 725.00 |
| Sodium dihydrogen phosphate | 598.00 |
| Sodium citrate hydrous | 300.00 |

This composition when dissolved in 9.1 ml. of water produced a clear solution with a pH of 3.5.

EXAMPLE XIII

A mixture of the following materials was prepared:

|  | Mgs. |
| --- | --- |
| Doxycycline hydrochloride | 635.00 |
| Magnesium chloride.4H$_2$O | 1,506.00 |
| Sodium dihydrogen phosphate | 1,367.00 |

This composition when dissolved in 8.1 ml. of water produced a clear solution having a pH of 2.0.

EXAMPLE XIV

A mixture of the following materials was prepared:

|  | Mgs. |
| --- | --- |
| Doxycycline hydrochloride | 635.00 |
| Magnesium chloride.4H$_2$O | 641.77 |
| Sodium dihydrogen phosphate | 529.70 |
| Ascorbic acid | 675.99 |
| Procaine hydrochloride | 200.00 |

This composition when dissolved in 9.1 ml. of water produced a clear solution with a pH of 2.0.

EXAMPLE XV

A mixture of the following materials was prepared:

|  | Mgs. |
| --- | --- |
| Doxycycline hydrochloride | 635.00 |
| Sodium dihydrogen phosphate | 853.8 |
| Magnesium sulfate, anhydrous | 744.8 |
| Lidocaine | 200.0 |
| Ascorbic acid | 762.8 |

When this composition is dissolved in 8.4 ml. of water, a clear solution containing 50 mg/ml of doxycycline activity and having a pH of 2.3 is produced.

EXAMPLE XVI

|  | Mg/Ml |
| --- | --- |
| Doxycycline hydrochloride | 126.957 |
| Phosphoric acid 85% | 167.95 |
| Magnesium oxide | 34.92 |
| Lidocaine | 20.00 |
| Monothioglycerol | 10.00 |
| Propyl gallate | 2.00 |
| Water for injection | 831.10 |

The doxycycline hydrochloride was added to the water with stirring. To this mixture was added the magnesium oxide and the pH was adjusted to 2.5 with the phosphoric acid. To this was then added the lidocaine, monothioglycerol and propyl gallate.

What I claim is:

1. A parenteral composition which when reconstituted with water forms a doxycycline chelate, said composition comprising a pharmaceutically acceptable acid addition salt of doxycycline, together with about 3 to 8 molar proportions of a water-soluble alkali metal phosphate salt per mole of said acid addition salt of doxycycline, wherein said alkali metal phosphate salt is sodium or potassium orthophosphate, metaphosphate, pyrophosphate, tripolyphosphate or hexametaphosphate and about 3 to 8 molar proportions of a pharmaceutically acceptable water-soluble magnesium salt per mole of said acid addition salt of doxycycline.

2. A composition as claimed in claim 1 wherein said doxycycline acid addition salt is doxycycline hydrochloride.

3. A composition as claimed in claim 1 wherein said alkali metal phosphate salt is sodium or potassium orthophosphate.

4. A composition as claimed in claim 1 wherein said pharmaceutically acceptable water-soluble magnesium salt is magnesium chloride, magnesium sulfate or magnesium gluconate.

5. A composition as claimed in claim 1 also containing sufficient water-soluble local anesthetic to provide up to about 2% weight volume upon reconstitution, said anesthetic being procaine, lidocaine or hydrochloride salts therof.

6. A doxycycline chelate composition for parenteral administration comprising a solution in water of from about 1 to 10% by weight of an antibiotic compound selected from doxycycline and the pharmaceutically acceptable acid addition salts thereof, together with per mole of said antibiotic compound about 3 to 8 molar proportions of a phosphate selected from phosphoric acid, sodium or potassium orthophosphate, metaphosphate, pyrophosphate, tripolyphosphate or hexametaphosphate, and about 3 to 8 molar proportions of a pharmaceutically acceptable magnesium salt soluble in said composition per mole of said antibiotic compound, said composition having a pH value in the range of from about 1.0 to 3.5.

7. A composition as claimed in claim 6 wherein said antibiotic compound is doxycycline hydrochloride.

8. A composition as claimed in claim 6 wherein said phosphate compound is phosphoric acid or sodium orthophosphate.

9. A composition as claimed in claim 6 wherein said magnesium compound is magnesium oxide or magnesium chloride.

10. A composition as claimed in claim 6 also containing up to about 2% weight volume of a local anesthetic wherein said anesthetic is selected from procaine, lidocaine and the hydrochloride salts thereof.

* * * * *